(12) United States Patent
Scaccabarozzi et al.

(10) Patent No.: US 8,405,825 B2
(45) Date of Patent: Mar. 26, 2013

(54) METHOD OF DETECTING A PARTICLE AND A LITHOGRAPHIC APPARATUS

(75) Inventors: Luigi Scaccabarozzi, Valkenswaard (NL); Vadim Yevgenyevich Banine, Deurne (NL); Christian Wagner, Duizel (NL)

(73) Assignee: ASML Netherlands B.V., Veldhoven (NL)

( * ) Notice: Subject to any disclaimer, the term of this patent is extended or adjusted under 35 U.S.C. 154(b) by 212 days.

(21) Appl. No.: 12/904,610

(22) Filed: Oct. 14, 2010

(65) Prior Publication Data
US 2011/0149276 A1 Jun. 23, 2011

Related U.S. Application Data

(60) Provisional application No. 61/287,399, filed on Dec. 17, 2009.

(51) Int. Cl.
*G01N 21/00* (2006.01)

(52) U.S. Cl. .................. 356/237.4; 356/237.3; 356/237.2
(58) Field of Classification Search ...... 356/237.1–237.5
See application file for complete search history.

(56) References Cited

U.S. PATENT DOCUMENTS

| 7,916,275 | B2 * | 3/2011 | De Mol et al. .................. 355/53 |
| 2007/0146695 | A1 * | 6/2007 | Brouwer et al. ........... 356/237.4 |

* cited by examiner

*Primary Examiner* — Michael P Stafira
(74) *Attorney, Agent, or Firm* — Sterne, Kessler, Goldstein & Fox P.L.L.C.

(57) ABSTRACT

A detector detects radiation from a mask to form an image, but the focal plane of the image is in front of the mask. Any particles arranged on the mask will be in focus. However, the pattern on the mask will be out of focus. It is therefore possible to detect the existence and location of particles on a mask having an arbitrary pattern. The depth of field of the detector is small and the focal plane is no further from the surface of the patterning device than two times the depth of field.

12 Claims, 4 Drawing Sheets

METHOD OF DETECTING A PARTICLE AND A LITHOGRAPHIC APPARATUS

CROSS REFERENCE TO RELATED APPLICATIONS

This application is claims benefit under 35 U.S.C. 119(e) to U.S. Provisional patent application No. 61/287,399, filed Dec. 17, 2009, which is incorporated by reference herein in its entirety.

BACKGROUND

1. Field of the Invention

The present invention relates to a lithographic apparatus and a method for manufacturing a device.

2. Background Art

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., comprising part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned.

Lithography is widely recognized as one of the key steps in the manufacture of ICs and other devices and/or structures. However, as the dimensions of features made using lithography become smaller, lithography is becoming a more critical factor for enabling miniature IC or other devices and/or structures to be manufactured.

A theoretical estimate of the limits of pattern printing can be given by the Rayleigh criterion for resolution as shown in equation (1):

$$CD = k_1 * \frac{\lambda}{NA} \quad (1)$$

where $\lambda$ is the wavelength of the radiation used, NA is the numerical aperture of the projection system used to print the pattern, k1 is a process dependent adjustment factor, also called the Rayleigh constant, and CD is the feature size (or critical dimension) of the printed feature. It follows from equation (1) that reduction of the minimum printable size of features can be obtained in three ways: by shortening the exposure wavelength $\lambda$, by increasing the numerical aperture NA or by decreasing the value of k1.

In order to shorten the exposure wavelength and, thus, reduce the minimum printable size, it has been proposed to use an extreme ultraviolet (EUV) radiation source. EUV radiation is electromagnetic radiation having a wavelength within the range of 10-20 nm, for example within the range of 13-14 nm. It has further been proposed that EUV radiation with a wavelength of less than 10 nm could be used, for example within the range of 5-10 nm such as 6.7 tun or 6.8 nm. Such radiation is termed extreme ultraviolet radiation or soft x-ray radiation. Possible sources include, for example, laser-produced plasma sources, discharge plasma sources, or sources based on synchrotron radiation provided by an electron storage ring.

EUV radiation may be produced using a plasma. A radiation system for producing EUV radiation may include a laser for exciting a fuel to provide the plasma, and a source collector module for containing the plasma. The plasma may be created, for example, by directing a laser beam at a fuel, such as particles of a suitable material (e.g., tin), or a stream of a suitable gas or vapor, such as Xe gas or Li vapor. The resulting plasma emits output radiation, e.g., EUV radiation, which is collected using a radiation collector. The radiation collector may be a mirrored normal incidence radiation collector, which receives the radiation and focuses the radiation into a beam. The source collector module may include an enclosing structure or chamber arranged to provide a vacuum environment to support the plasma. Such a radiation system is typically termed a laser produced plasma (LPP) source.

Although lithographic apparatus are generally operated with a pellicle to protect the mask no pellicle is used in EUV lithographic apparatus in order to avoid absorption of the radiation beam. This leaves the mask open to contamination by organic and inorganic particles. In particular, debris particles in the system may originate from the plasma source used to generate the EUV radiation. To avoid defects in the resulting patterned devices it is necessary to ensure that the mask is free from contamination and conventionally this is achieved by inspection. As the pattern is arbitrary, a printed pattern is generally compared with another printed pattern. Inspecting patterns is slow, taking up to 4 hours per mask and thus expensive. Furthermore, a particle may scatter radiation in the same way as the pattern on the device so it is difficult to distinguish between radiation scattered by the arbitrary pattern and radiation scattered by a particle on the pattern if a comparison between light scattered from the clean mask and light scattered from a dirty mask is not done.

SUMMARY

It is desirable to provide a fast method of detecting a particle on an arbitrary pattern.

According to an aspect of the present invention, there is provided a lithographic apparatus comprising an illumination system, a support, a substrate table, a projection system, and a detector. The illumination system is configured to condition a beam of EUV radiation. The support is constructed to support a patterning device, the patterning device being capable of imparting the radiation beam with a pattern in its cross-section to form a patterned radiation beam. The substrate table is constructed to hold a substrate. The projection system is configured to project the patterned radiation beam onto a target portion of the substrate. The detector is configured to detect radiation from the patterning device to form an image, the detector having a depth of field and the image being optically conjugate to an object focal plane, wherein the object focal plane is in front of the surface of the patterning device and between 0.5-2 times the depth of field away from the surface of the patterning device.

According to a further aspect of the invention, there is provided a method of detecting particles on a patterning device in an EUV lithographic apparatus, the method comprising the following steps (not necessarily in the order shown). Detecting radiation from the patterning device to form a first image using a detector. The image being optically conjugate to an object focal plane, and the detector having a depth of field. The object focal plane is in front of the surface of the patterning device and between 0.5-2 times the depth of field away from the surface of the patterning device.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated herein and form part of the specification, illustrate the present invention and, together with the description, further serve to explain the principles of the invention and to enable a person skilled in the relevant art(s) to make and use the invention

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION

This specification discloses one or more embodiments that incorporate the features of this invention. The disclosed embodiment(s) merely exemplify the invention. The scope of the invention is not limited to the disclosed embodiment(s). The invention is defined by the claims appended hereto.

The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Embodiments of the invention may be implemented in hardware, firmware, software, or any combination thereof. Embodiments of the invention may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc.

Before describing such embodiments in more detail, however, it is instructive to present an example environment in which embodiments of the present invention may be implemented.

Figure 1:
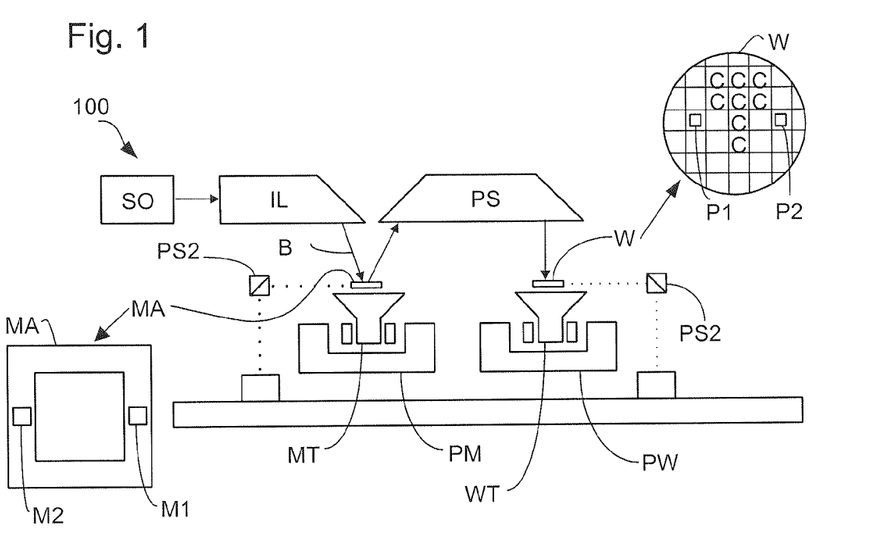
FIG. 1 depicts a lithographic apparatus according to an embodiment of the invention.

FIG. 1 schematically depicts a lithographic apparatus 100 including a source collector module SO according to one embodiment of the invention. The apparatus comprises: an illumination system (illuminator) IL configured to condition a radiation beam B (e.g., EUV radiation). a support structure (e.g., a mask table) MT constructed to support a patterning device (e.g., a mask or a reticle) MA and connected to a first positioner PM configured to accurately position the patterning device; a substrate table (e.g., a wafer table) WT constructed to hold a substrate (e.g., a resist coated wafer) W and connected to a second positioner PW configured to accurately position the substrate; and a projection system (e.g., a reflective projection system) PS configured to project a pattern imparted to the radiation beam B by patterning device MA onto a target portion C (e.g., comprising one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure MT holds the patterning device MA in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system.

The term "patterning device" should be broadly interpreted as referring to any device that can be used to impart a radiation beam with a pattern in its cross-section such as to create a pattern in a target portion of the substrate. The pattern imparted to the radiation beam may correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The projection system, like the illumination system, may include various types of optical components, such as refractive, reflective, magnetic, electromagnetic, electrostatic or other types of optical components, or any combination thereof, as appropriate for the exposure radiation being used, or for other factors such as the use of a vacuum. It may be desired to use a vacuum for EUV radiation since other gases may absorb too much radiation. A vacuum environment may therefore be provided to the whole beam path with the aid of a vacuum wall and vacuum pumps.

As here depicted, the apparatus is of a reflective type (e.g., employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

Referring to FIG. 1, the illuminator IL receives an extreme ultra violet radiation beam from the source collector module SO. Methods to produce EUV light include, but are not necessarily limited to, converting a material into a plasma state that has at least one element, e.g., xenon, lithium or tin, with one or more emission lines in the EUV range. In one such method, often termed laser produced plasma ("LPP") the required plasma can be produced by irradiating a fuel, such as a droplet, stream or cluster of material having the required line-emitting element, with a laser beam. The source collector module SO may be part of an EUV radiation system including a laser, not shown in FIG. 1, for providing the laser beam exciting the fuel. The resulting plasma emits output radiation, e.g., EUV radiation, which is collected using a radiation collector, disposed in the source collector module. The laser and the source collector module may be separate entities, for example when a CO2 laser is used to provide the laser beam for fuel excitation.

In such cases, the laser is not considered to form part of the lithographic apparatus and the radiation beam is passed from the laser to the source collector module with the aid of a beam delivery system comprising, for example, suitable directing mirrors and/or a beam expander. In other cases the source may be an integral part of the source collector module, for example when the source is a discharge produced plasma EUV generator, often termed as a DPP source.

The illuminator IL may comprise an adjuster for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as facetted field and pupil mirror devices. The illuminator may be used to condition the radiation beam, to have a desired uniformity and intensity distribution in its cross section.

The radiation beam B is incident on the patterning device (e.g., mask) MA, which is held on the support structure (e.g., mask table) MT, and is patterned by the patterning device. After being reflected from the patterning device (e.g., mask) MA, the radiation beam B passes through the projection system PS, which focuses the beam onto a target portion C of the substrate W. With the aid of the second positioner PW and position sensor PS2 (e.g., an interferometric device, linear encoder or capacitive sensor), the substrate table WT can be moved accurately, e.g., so as to position different target portions C in the path of the radiation beam B. Similarly, the first positioner PM and another position sensor PS1 can be used to accurately position the patterning device (e.g., mask) MA with respect to the path of the radiation beam B. Patterning device (e.g., mask) MA and substrate W may be aligned using mask alignment marks M1, M2 and substrate alignment marks P1, P2.

The depicted apparatus could be used in at least one of the following modes:

1. In step mode, the support structure (e.g., mask table) MT and the substrate table WT are kept essentially stationary, while an entire pattern imparted to the radiation beam is projected onto a target portion C at one time (i.e., a single static exposure). The substrate table WT is then shifted in the X and/or Y direction so that a different target portion C can be exposed.

2. In scan mode, the support structure (e.g., mask table) MT and the substrate table WT are scanned synchronously while a pattern imparted to the radiation beam is projected onto a target portion C (i.e., a single dynamic exposure). The velocity and direction of the substrate table WT relative to the support structure (e.g., mask table) MT may be determined by the (de-)magnification and image reversal characteristics of the projection system PS.

3. In another mode, the support structure (e.g., mask table) MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
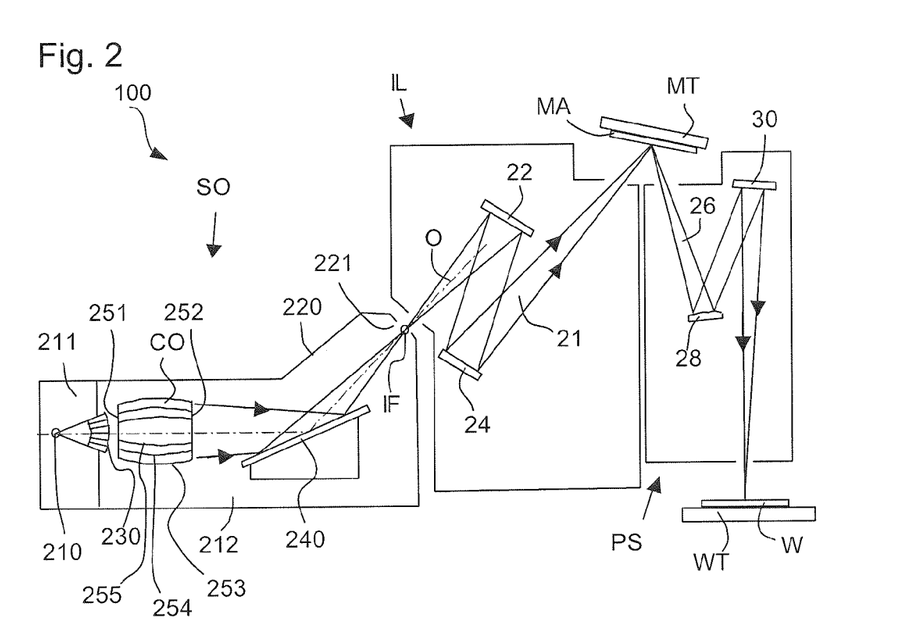
FIG. 2 is a more detailed view of the apparatus of FIG. 1.

FIG. 2 shows the apparatus 100 in more detail, including the source collector module SO, the illumination system IL, and the projection system PS. The source collector module SO is constructed and arranged such that a vacuum environment can be maintained in an enclosing structure 220 of the source collector module SO. An EUV radiation emitting plasma 210 may be formed by a discharge produced plasma source. EUV radiation may be produced by a gas or vapor, for example Xe gas, Li vapor or Sn vapor in which the very hot plasma 210 is created to emit radiation in the EUV range of the electromagnetic spectrum. The very hot plasma 210 is created by, for example, an electrical discharge causing an at least partially ionized plasma. Partial pressures of, for example, 10 Pa of Xe, Li, Sn vapor or any other suitable gas or vapor may be required for efficient generation of the radiation. In an embodiment, a plasma of excited tin (Sn) is provided to produce EUV radiation.

The radiation emitted by the hot plasma 210 is passed from a source chamber 211 into a collector chamber 212 via an optional gas barrier or contaminant trap 230 (in some cases also referred to as contaminant barrier or foil trap) which is positioned in or behind an opening in source chamber 211. The contaminant trap 230 may include a channel structure. Contamination trap 230 may also include a gas barrier or a combination of a gas barrier and a channel structure. The contaminant trap or contaminant barrier 230 further indicated herein at least includes a channel structure, as known in the art.

The collector chamber 211 may include a radiation collector CO that may be a so-called grazing incidence collector. Radiation collector CO has an upstream radiation collector side 251 and a downstream radiation collector side 252.

Radiation that traverses collector CO can be reflected off a grating spectral filter 240 to be focused in a virtual source point IF. The virtual source point IF is commonly referred to as the intermediate focus, and the source collector module is arranged such that the intermediate focus IF is located at or near an opening 221 in the enclosing structure 220. The virtual source point IF is an image of the radiation emitting plasma 210.

Subsequently the radiation traverses the illumination system IL, which may include a facetted field minor device 22, and a facetted pupil mirror device 24 arranged to provide a desired angular distribution of the radiation beam 21, at the patterning device MA, as well as a desired uniformity of radiation intensity at the patterning device MA. Upon reflection of the beam of radiation 21 at the patterning device MA, held by the support structure MT, a patterned beam 26 is formed and the patterned beam 26 is imaged by the projection system PS via reflective elements 28, onto a substrate W held by the wafer stage or substrate table WT.

More elements than shown may generally be present in illumination optics unit IL and projection system PS. The grating spectral filter 240 may optionally be present, depending upon the type of lithographic apparatus. Further, there may be more minors present than those shown in the Figures, for example there may be 1-6 additional reflective elements present in the projection system PS than shown in FIG. 2.

Collector optic CO, as illustrated in FIG. 2, is depicted as a nested collector with grazing incidence reflectors 253, 254 and 255, just as an example of a collector (or collector mirror). The grazing incidence reflectors 253, 254 and 255 are disposed axially symmetric around an optical axis O and a collector optic CO of this type is preferably used in combination with a discharge produced plasma source, often called a DPP source.

Figure 3:
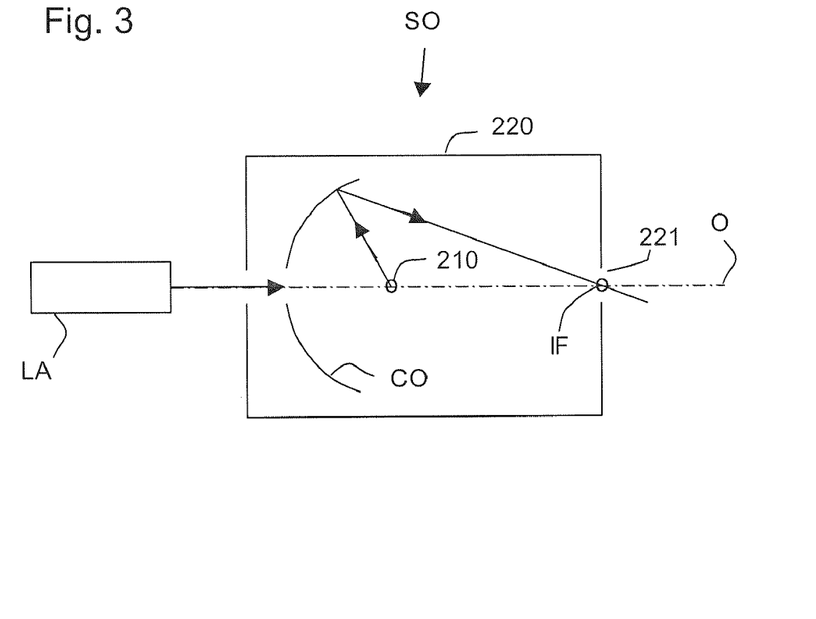
FIG. 3 is a more detailed view of the source collector module of the apparatus of FIGS. 1 and 2.

Alternatively, the source collector module SO may be part of an LPP radiation system as shown in FIG. 3. A laser LA is arranged to deposit laser energy into a fuel, such as xenon (Xe), tin (Sn) or lithium (Li), creating the highly ionized plasma 210 with electron temperatures of several 10's of eV. The energetic radiation generated during de-excitation and recombination of these ions is emitted from the plasma, collected by a near normal incidence collector optic CO and focused onto the opening 221 in the enclosing structure 220.

Figure 4:
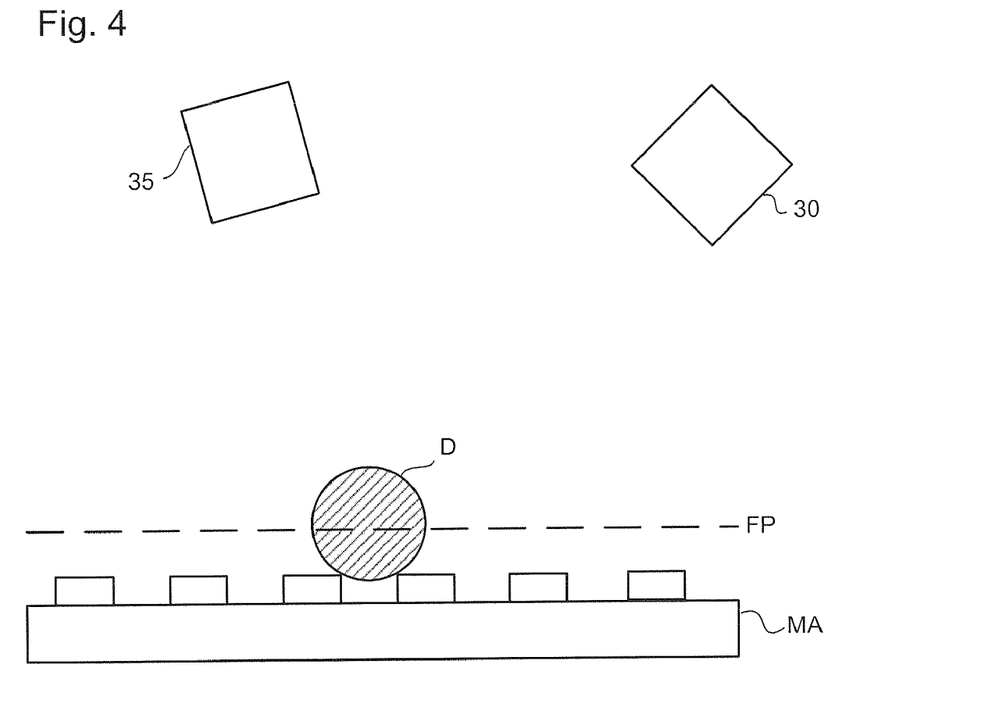
FIG. 4 is a cross section of a particle and patterning device.

According to an embodiment of the present invention, radiation from the mask MA is detected using a camera 30 to form an image. However, as shown in FIG. 4, the (object) focal plane FP of the image is in front of the surface of the mask MA. Thus any particles, D, will be detected. Although the pattern will also be detected, it will form part of the background noise as it is out of focus, whereas at least part of the particle D is in focus. The results can be seen in FIG. 5 in which the particles, D are shown as bright spots whereas the pattern shows up simply as background noise. It may also be possible to minimize the effect of the background pattern by applying a filter. For best results, the focal plane should be in front of the surface of the mask and approximately a depth of field away from the surface of the mask, where the depth of field is $0.5\lambda/NA^2$. The focal plane should preferably be 0.5-2 times the depth of field away from the surface of the mask, and more preferably 0.5-1 times the depth of field away from the surface of the mask.

For the technique to be as sensitive as possible, the depth of field should be minimized. Thus the numerical aperture should preferably be as large as possible and the wavelength of the radiation detected as short as possible, preferably 450-500 nm. To detect 1 μm particles using radiation of 400-500 nm the numerical aperture should be >0.6. To detect 0.5 μm particles using similar radiation the numerical aperture should be >0.9.

In order to obtain a clearer image of the mask it may be illuminated using a source 35, which preferably emits radiation within the range 450-500 nm.

The mask MA may be scanned in two different modes. Firstly, the focal plane may be kept at a fixed distance from the mask. Secondly, the position of the focal plane relative to the mask may be moved varied. This may be achieved by adjusting the optical components of the camera, adjusting the location of the camera or adjusting the location of the mask. Several images may therefore be acquired and can be compared to determine the location of particles. The second method has the advantage that it may detect particles of different sizes and smaller particles.

Figure 5:
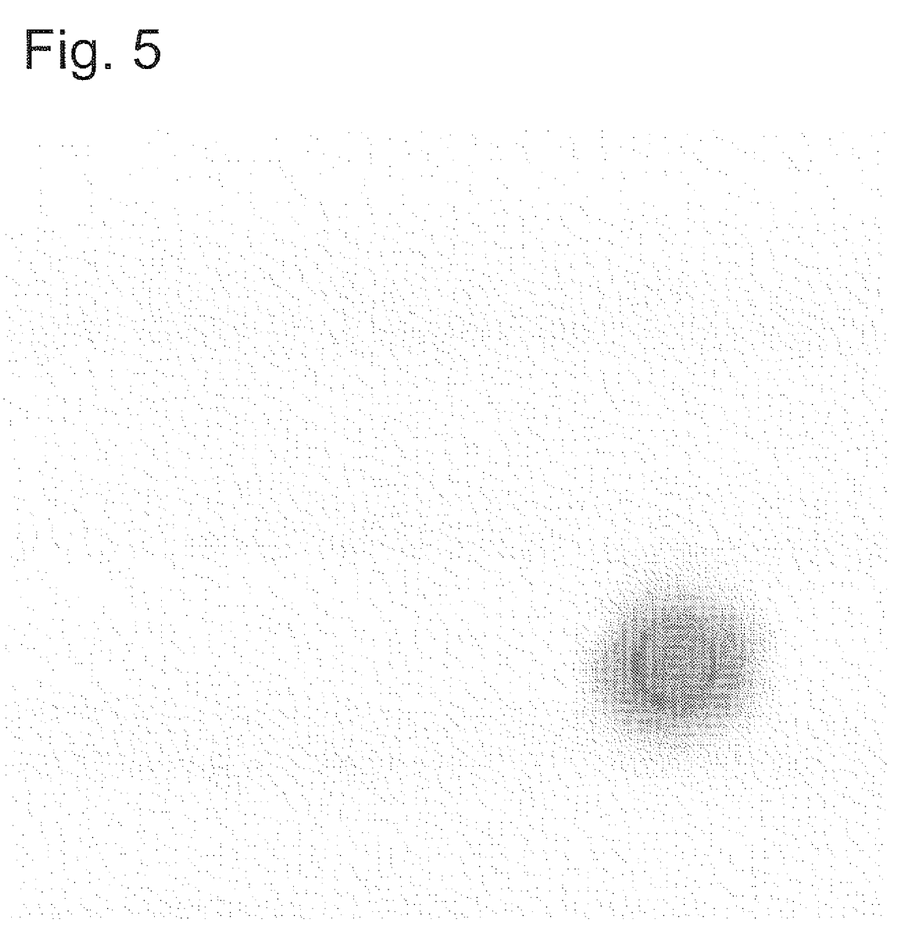
FIG. 5 depicts an image detected, using a method according to an embodiment of the invention.

A quick visual inspection of the image depicted in FIG. 5 will show the location of any particles. Alternatively, any method which determines images using, for example, a minimum intensity threshold may be used. If the mask MA is clean production can continue and if dust particles are detected the mask can be cleaned. The present invention provides a quick and cheap method to detect dust particles. Furthermore, the apparatus used is relatively cheap and simple to incorporate into a lithographic apparatus.

Figure 6A:
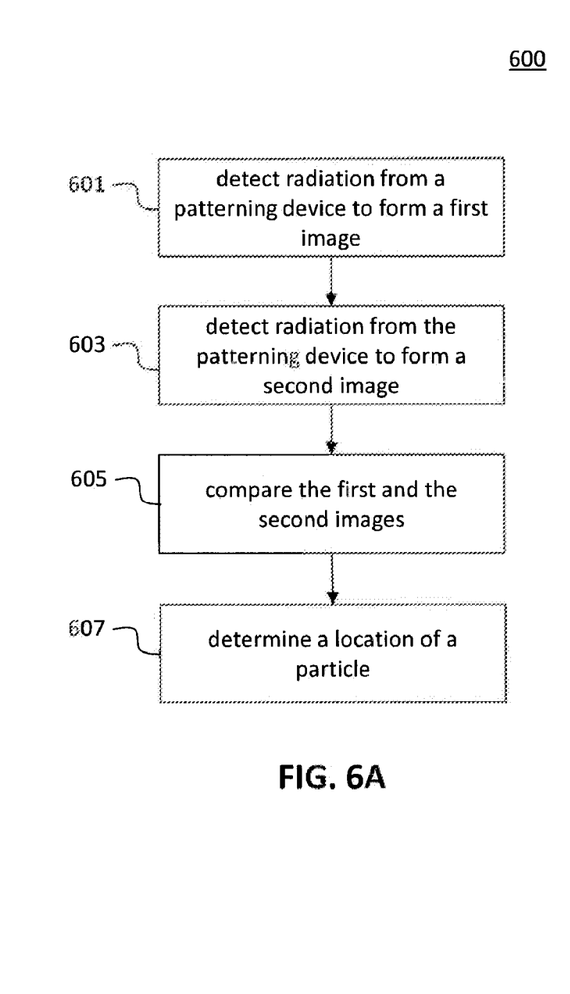
FIGS. 6A and 6B illustrate flow diagrams illustrating example methods for detecting particles, according to another embodiment.

FIG. 6A is a flowchart depicting a method 600, according to an embodiment. For example, method 600 can efficiently detect particles. In one example, method 600 is performed by the device depicted in FIG. 4. It is to be appreciated not all steps may be needed or performed in the order shown in FIG. 6A. Reference is made to the device depicted in FIG. 4 merely for convenience of discussion. Other system may be used to perform the method.

In step 601, a radiation from a patterning device, such as mask MA of FIG. 4, is detected to form a first image. In step 603, a second image can be formed by detecting radiation from the patterning device. In step 605, the first image and the second image are compared such that any particle on the patterning device can be located at step 607. The focal plane may be kept at a fixed distance from the patterning device or the position of the focal plane relative to the patterning device may be moved varied.

Figure 6B:
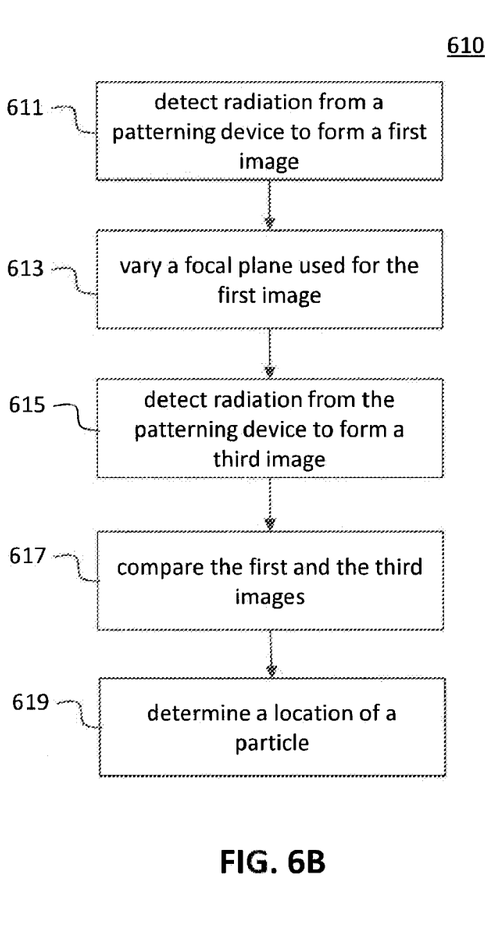

FIG. 6B is a flowchart depicting a method 610, according to an embodiment. For example, method 610 can also efficiently detect particles. In one example, method 610 is performed by the device depicted in FIG. 4. It is to be appreciated not all steps may be needed or performed in the order shown in FIG. 6B. Reference is made to the device depicted in FIG. 4 merely for convenience of discussion. Other system may be used to perform the method.

In step 611, a radiation from a patterning device, such as mask MA of FIG. 4, is detected to form a first image. In step 613, the position of the focal plane relative to the patterning device is varied. In step 615, a third image can be formed by detecting radiation from the patterning device. In step 617, the first image and the third image are compared such that any particle on the patterning device can be located at step 619.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that an embodiment of the present invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The term "lens", where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. For example, the invention may take the form of a computer program containing one or more sequences of machine-readable instructions describing a method as disclosed above, or a data storage medium (e.g., semiconductor memory, magnetic or optical disk) having such a computer program stored therein. The descriptions above are intended to be illustrative, not limiting. Thus it will be apparent to one skilled in the art that modifications may be made to the invention as described without departing from the scope of the claims set out below.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The claims in the instant application are different than those of the parent application or other related applications. The Applicant therefore rescinds any disclaimer of claim scope made in the parent application or any predecessor application in relation to the instant application. The Examiner is therefore advised that any such previous disclaimer and the cited references that it was made to avoid, may need to be revisited. Further, the Examiner is also reminded that any disclaimer made in the instant application should not be read into or against the parent application.

What is claimed is:

1. A lithographic apparatus comprising:
    an illumination system configured to condition a beam of EUV radiation;
    a support constructed to support a patterning device, the patterning device being capable of imparting the radiation beam with a pattern in its cross-section to form a patterned radiation beam;
    a substrate table constructed to hold a substrate;
    a projection system configured to project the patterned radiation beam onto a target portion of the substrate; and
    a detector configured to detect radiation from the patterning device to form an image, the detector having a depth of field and the image being optically conjugate to an object focal plane, wherein the object focal plane is in front of the surface of the patterning device and between approximately 0.5-2 times the depth of field away from the surface of the patterning device.

2. The lithographic apparatus according to claim 1, wherein the detector has a numerical aperture of greater than about 0.6.

3. The lithographic apparatus according to either claim 1, wherein the radiation detected has a wavelength approximately 450-500 nm.

4. The lithographic apparatus according to claim 1, wherein the patterning device comprises a reflective patterning device.

5. The lithographic apparatus according to claim 1, wherein the position of the focal plane of the detector is adjustable.

6. The lithographic apparatus according to claim 1, further comprising a radiation source configured to illuminate the patterning device with radiation having a wavelength approximately 450-500 nm.

7. A method of detecting particles on a patterning device in an EUV lithographic apparatus, the method comprising:
    detecting radiation from the patterning device to form a first image using a detector, the image being optically conjugate to an object focal plane, and the detector having a depth of field,
    wherein the object focal plane is in front of the surface of the patterning device and between approximately 0.5-2 times the depth of field away from the surface of the patterning device.

8. The method according to claim 7, further comprising detecting radiation from the patterning device to form a second image, the focal plane of the second image being the surface of the patterning device.

9. The method according to claim 8, further comprising comparing the first and second image.

10. The method according to claim 7, further comprising detecting radiation from the patterning device to form a third image, the focal plane of the third image being different from the first focal plane, and being between the surface of the patterning device and a depth of field of the radiation beam away from the patterning device.

11. The method according to claim 7, wherein the detector detects radiation having a wavelength about 450-500 nm.

12. The method according to claim 7, farther comprising using a reflective patterning device for the patterning device.

* * * * *